(12) United States Patent
Moore, Jr. et al.

(10) Patent No.: US 9,012,684 B2
(45) Date of Patent: Apr. 21, 2015

(54) AMINOCARBOXYLATE POWDERS WITH IMPROVED PURITY AND FLOWABILITY PROPERTIES

(75) Inventors: J. Weldon Moore, Jr., Lake Jackson, TX (US); Steven T. Booth, Wilmington, DE (US); Ray O. Leenhouts, Midland, TX (US)

(73) Assignee: Dow Global Technologies LLC

( * ) Notice: Subject to any disclaimer, the term of this patent is extended or adjusted under 35 U.S.C. 154(b) by 667 days.

(21) Appl. No.: 13/110,318

(22) Filed: May 18, 2011

(65) Prior Publication Data

US 2011/0288332 A1 Nov. 24, 2011

Related U.S. Application Data

(60) Provisional application No. 61/346,960, filed on May 21, 2010.

(51) Int. Cl.
| | | |
|---|---|---|
| C07C 227/00 | (2006.01) |
| C07C 229/30 | (2006.01) |
| C07C 227/26 | (2006.01) |
| C07C 227/42 | (2006.01) |
| C07C 227/44 | (2006.01) |

(52) U.S. Cl.
CPC ......... *C07C 227/26* (2013.01); *C07C 227/42* (2013.01); *C07C 227/44* (2013.01)

(58) Field of Classification Search
USPC .................................. 562/554, 566
See application file for complete search history.

(56) References Cited

U.S. PATENT DOCUMENTS

| | | | |
|---|---|---|---|
| 2,407,645 A | 9/1946 | Bersworth | |
| 2,500,019 A | 3/1950 | Bersworth | |
| 2,906,762 A | 9/1959 | Knell et al. | |
| 3,607,931 A * | 9/1971 | Hegarty et al. | 562/566 |
| 3,668,246 A | 6/1972 | Berding et al. | |
| 3,681,416 A | 8/1972 | Miller et al. | |
| 4,636,336 A | 1/1987 | Gay et al. | |
| 5,110,965 A | 5/1992 | Thunberg et al. | |
| 5,958,866 A | 9/1999 | Donoghue et al. | |
| 6,451,224 B1 | 9/2002 | Wilson | |
| 7,034,172 B1 | 4/2006 | Friedrich | |
| 7,105,176 B2 | 9/2006 | Auweter et al. | |
| 2008/0045430 A1 | 2/2008 | Witteler et al. | |
| 2011/0004016 A1 | 1/2011 | Oftring et al. | |

FOREIGN PATENT DOCUMENTS

| | | |
|---|---|---|
| DE | 89849 | 5/1972 |
| DE | 4211713 A1 | 10/1993 |
| DE | 19937345 A1 | 2/2001 |
| GB | 136099 | 1/1920 |
| JP | 11124595 A | 5/1999 |
| JP | 1999124595 | 11/1999 |
| RO | 85562 | 2/1985 |
| WO | 00/12463 A1 | 3/2000 |
| WO | 2004/067603 A1 | 8/2004 |
| WO | 2009/024518 A1 | 2/2009 |

OTHER PUBLICATIONS

International Search Report and Written Opinion to PCT/US2011/036948 dated Nov. 18, 2011.

* cited by examiner

*Primary Examiner* — Paul A Zucker
*Assistant Examiner* — Mark Luderer

(57) ABSTRACT

Provided is a method for preparing stable free flowing solid aminocarboxylate chelants by adding to a chelant that contains residual alkaline metal hydroxide a free or partially neutralized carboxylic acid such that the free or partially neutralized acid neutralizes at least a portion of the alkaline metal hydroxide; and isolating therefrom the free-flowing solid chelant.

9 Claims, 1 Drawing Sheet

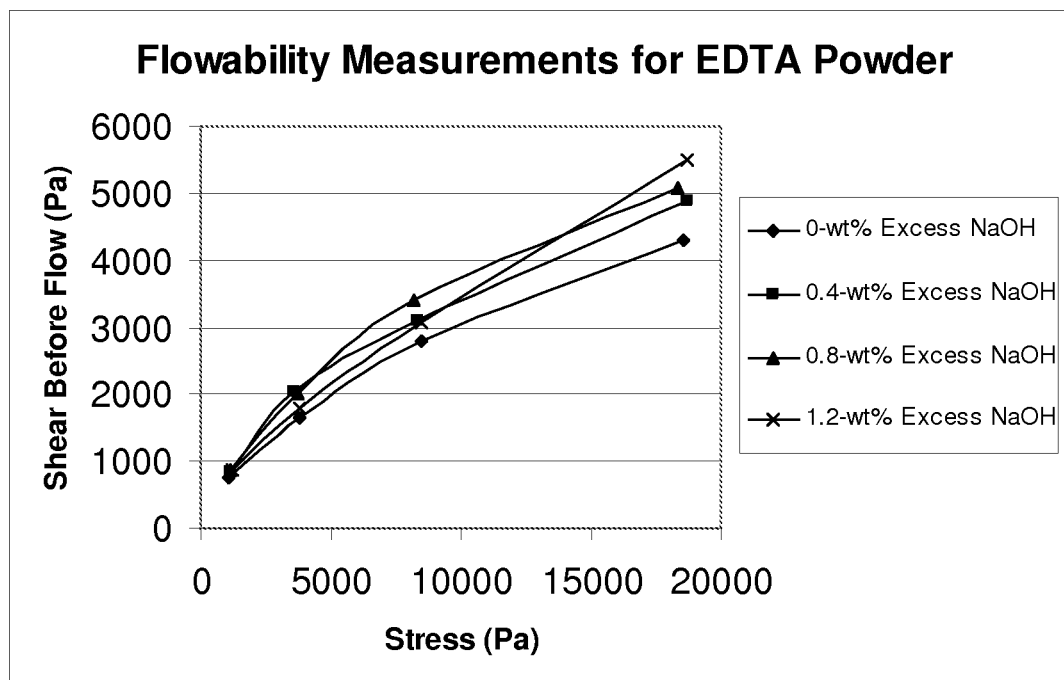

AMINOCARBOXYLATE POWDERS WITH IMPROVED PURITY AND FLOWABILITY PROPERTIES

This application claims priority to U.S. provisional application Ser. No. 61/346,960, filed May 21, 2010, which is incorporated herein by reference in its entirety.

FIELD OF THE INVENTION

The invention relates to processes for preparing stable free flowing solid chelants.

BACKGROUND OF THE INVENTION

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Commercially available chelants are typically aqueous solutions having a chelant activity of about 40 percent to about 60 percent by weight.

Aminocarboxylic acid chelants and their salts (aminocarboxylates) may be prepared by a number of known techniques. On an industrial scale, a typical process involves the reaction of an amine with formaldehyde and cyanide in the presence of an alkaline metal hydroxide (see e.g., Bersworth, U.S. Pat. No. 2,407,645, which is incorporated herein by reference).

There are various disadvantages associated with the known manufacturing processes. One such disadvantage is that chelants produced by methods that utilize an alkaline metal hydroxide as a reagent, including the Bersworth process described above, in general are hygroscopic and become caked when exposed to the atmosphere. Chelants with better atmospheric stability and solid flowability are desirable in the industry.

BRIEF SUMMARY OF THE INVENTION

The invention provides a method for producing a solid aminocarboxylate chelant which is low hygroscopic and remains free-flowing when exposed to the atmosphere. The method comprises: (a) providing a solution comprising the aminocarboxylate chelant and residual alkaline metal hydroxide; (b) adding to the solution a free or partially neutralized carboxylic acid such that the free or partially neutralized acid neutralizes at least a portion of the residual alkaline metal hydroxide; and (c) isolating therefrom the free-flowing solid aminocarboxylate chelant.

DESCRIPTION OF THE FIGURES

FIG. 1 is a graph showing flowability measurements for EDTA powders containing various NaOH concentrations.

DETAILED DESCRIPTION OF THE INVENTION

As noted above, the invention provides a method for producing a free-flowing solid aminocarboxylate chelant. Any aminocarboxylate chelant that contains residual excess alkaline metal hydroxide (e.g., sodium hydroxide or potassium hydroxide) may suitably be used in the method of the invention. As noted, chelants manufactured by processes that utilize an alkaline metal hydroxide as a reagent typically contain residual amounts of the reagent and as such are particularly suited for the invention. Non-limiting examples of these manufacturing processes include, for instance, the Bersworth process and the low NTA process of the second aspect of the invention, described in more detail below.

In step (a) of the method, a fully neutralized aminocarboxylate chelant containing residual alkaline metal hydroxide is provided as an aqueous solution. In some embodiments, the solution may contain between 20 and 70 percent, alternatively, between 30 and 60 percent, by weight of the aminocarboxylate chelant based on the total weight of the solution. The solution may contain greater than 0%, alternatively at least 0.1%, alternatively at least 0.8%, or alternatively at least 1.2% by weight of the alkaline metal hydroxide, based on the total weight of the solution. In some embodiments, the solution may contain up to 5%, alternatively up to 2% by weight of the alkaline metal hydroxide, based on the total weight of the solution.

As noted, any aminocarboxylate chelant that contains residual alkaline metal hydroxide may be used in the invention. Examples include the full alkaline metal salts of: ethylenediamine-N,N,N',N'-tetraacetic acid (EDTA); 1,1,4,7,7-diethylene-triaminepentaacetic acid (DTPA); ethylenediamine-N,N'-disuccinic acid (EDDS); (2-hydroxyethyl)-imino-diacetic acid (HEIDA); L-glutamic acid-N,N-di-(acetic acid) (GLDA); ethylenediamine-N,N'-diacetic acid (EDDA); or hydroxyethylethylene-diaminotriacetic acid (HEDTA). Suitable alkaline metals for the salts include sodium and potassium, with sodium being preferred.

In step (b) of the method, a molecule containing a free or partially neutralized carboxylic acid is added to the solution. Sufficient free or partially neutralized carboxylic acid is used such that the acid reacts with at least a portion of the residual alkaline metal hydroxide, thereby reducing the levels of the metal hydroxide. The amount of free or partially neutralized carboxylic acid that should be used can be readily determined by a person of ordinary skill in the art and will depend, for instance, on how much alkaline metal hydroxide is present, the number of available acid groups in the free or partially neutralized carboxylic acid, and how much of the hydroxide it is desired to neutralize. By way of example, in the case of EDTA, 1 mole of ethylenediamine-N,N,N',N'-tetraacetic acid (EDTA) may be used to neutralize 4 moles of residual sodium hydroxide (NaOH).

In some embodiments, it is desirable to add sufficient free or partially neutralized carboxylic acid in order to reduce the level of alkaline metal salt to 5% or less, alternatively 2% or less, alternatively 1.2% or less, alternatively 0.8% or less, alternatively 0.5% or less, or alternatively 0.1% or less, by weight based on the total weight of the solution.

It is also preferred that sufficient free or partially neutralized acid be added as described above, but without significantly acidifying the aminocarboxylate chelant in the solution. In some embodiments, the amount of free or partially neutralized acid used is such that no more than 5%, alternatively no more than 2%, alternatively no more than 1%, or alternatively no more than 0.1% by weight of the aminocarboxylate is acidified. It is also preferable that the pH of the solution, during and following addition of the carboxylic acid, does not drop below 7 (i.e., the pH is 7 or greater).

Examples of suitable carboxylic acids for use in step (b) include, but are not limited to, oxalic acid, glycolic acid, and formic acid. Also suitable are free or partially neutralized aminocarboxylic acid chelants, such as the free or partially neutralized acids of: ethylenediamine-N,N,N',N'-tetraacetic acid (EDTA); 1,1,4,7,7-diethylene-triaminepentaacetic acid (DTPA); ethylenediamine-N,N'-disuccinic acid (EDDS);

(2-hydroxyethyl)-imino-diacetic acid (HEIDA); L-glutamic acid-N,N-di-(acetic acid) (GLDA); ethylenediamine-N,N'-diacetic acid (EDDA); or hydroxyethylethylene-diaminotri-acetic acid (HEDTA). Where the material is partially neutralized, suitable salts include the sodium and potassium salts, with sodium being preferred.

In a particular embodiment, an aminocarboxylic acid is used in step (b) that is the free acid or partially neutralized salt of (i.e., corresponding to) the aminocarboxylate being treated. Thus, for instance, if the aminocarboxylate is tetrasodium EDTA, then a suitable aminocarboxylic acid under this embodiment may be EDTA or $Na_2EDTA$.

It is not required, however, under the invention for the free or partially neutralized aminocarboxylic acid to correspond to the aminocarboxylate and in some embodiments it may be preferable for them not to correspond. For instance, if the aminocarboxylate is a relatively expensive material, use of a different free or partially neutralized acid that is less costly may be preferred.

The mixture, containing the free or partially neutralized acid, the aminocarboxylate, and the alkaline metal hydroxide may be heated to, for example, between 45° C. and 100° C., in order to facilitate the neutralization reaction. Heating, however, is not required. The mixture may also be stirred, also to facilitate the reaction.

In step (c) of the method, once sufficient time for the neutralization of the alkaline metal hydroxide has elapsed, which, in some embodiments, may be between 5 min and 4 hours, the purified aminocarboxylate chelant may then be isolated from the mixture as a free-flowing solid. Various isolation techniques and combinations of techniques may be used including, for instance, crystallization or drying.

In crystallization, typically the aminocarboxylate solution is evaporated beyond its saturation point, allowing for a portion of the aminocarboxylate to crystallize in a solid form which can be recovered. This is typically achieved by driving off water by heating the aminocarboxylate solution.

Drying of the aminocarboxylate solution may be done by any conventional drying method. For instance, the drying may conveniently be done in a vacuum oven at suitably elevated temperature or by spraying the aminocarboxylate chelant solution into a conventional counter-current or co-current spray-drying tower. In the spray drying tower, water is evaporated by hot gas, usually hot air, to such an extent that a solid aminocarboxylate chelant is obtained in a powder or granular form. Examples of other drying techniques that may be used include rotating disk drying, rotating drum drying, or freeze drying.

In an exemplary embodiment, the method of the invention is used to produce free-flowing solid ethylenediamine-N,N,N',N'-tetraacetic acid tetrasodium salt ($Na_4EDTA$). The method comprises: (a) providing a solution comprising the ethylenediamine-N,N,N',N'-tetraacetic acid tetrasodium salt and sodium hydroxide; (b) adding to the solution ethylenediamine-N-N,N',N'-tetraacetic acid or a partial salt thereof such that at least a portion of the sodium hydroxide is neutralized; and (c) isolating therefrom the free-flowing solid ethylenediamine-N,N,N',N'-tetraacetic acid tetrasodium salt by crystallization or spray-drying. In a further embodiment, the acid or salt of step (b) comprises ethylenediamine-N,N,N',N'-tetraacetic acid, alternatively ethylenediamine-N,N,N',N'-tetraacetic acid monosodium salt, alternatively ethylenediamine-N,N,N',N'-tetraacetic acid disodium salt, alternatively ethylenediamine-N,N,N',N'-tetraacetic acid trisodium salt, or alternatively a mixture of two or more of the foregoing.

In a second aspect, the invention provides a method for preparing an aminocarboxylic acid or salt thereof (aminocarboxylate) chelant containing low levels of nitrilotriacetic acid. Chelants produced by conventional processes utilizing cyanide and formaldehyde, including the Bersworth process described above, may be contaminated with nitrilotriacetic acid or its salts (NTA). NTA is an undesirable impurity in the final product and its levels are increasingly subject to government regulation in some regions. Thus, chelants that contain little or no NTA are desirable.

The invention addresses the problem of NTA contamination by providing a method in which an amine precursor of the desired aminocarboxylic acid is reacted with formaldehyde and cyanide in the presence of a base in sufficient amounts and under conditions to form the chelant. The reaction between the cyanide, formaldehyde and precursor amine is carried under various protocols that result in significantly reduced formation of NTA or its salts.

Under one such protocol, the formaldehyde and cyanide are added substantially over the whole reaction (the time required for the reaction to go to substantial completion). In some embodiments, the formaldehyde and cyanide are added over a period of between 4 and 24 hours. Further, a profiled addition rate of the formaldehyde and cyanide may be used such that the rate during the first half of the reaction is on average greater than during the second half of the reaction. For example, in some embodiments, in a reaction whose reaction time is about six hours, about half of the formaldehyde and cyanide are added over 2 hours during the first half of the reaction, and the remainder added over 4 hours during the second half of the reaction.

A further protocol for reducing NTA levels in the chelant product is that byproduct ammonia is continuously removed from the reaction substantially as it is formed. Various techniques may be used for ammonia removal including, for instance, distillation or gas (e.g., air or steam) stripping. In some embodiments, a gas:amine purge rate of 1 to 50 mol gas to mol amine may be used.

Because byproducts of cyanide and formaldehyde can be formed in the reaction, the exact ratio of cyanide/formaldehyde to amine will vary. The general ratio of cyanide/formaldehyde to amine is related to the reactivity of the amine and the base concentration. Slower reactive amines and higher caustic levels generally result in more glycolate or formate byproducts.

For example, in some embodiments, a ratio of reactive cyanide/formaldehyde (defined as any cyanide/formaldehyde that is not reduced to glycolate or formate salts in the reaction) to amine group of 1.60-2.0, alternatively 1.90-2.0, or alternatively 2.0 may be used is for forming EDTA with low NTA levels. When making GLDA, a ratio of 2.5-3, alternatively 2.7 cyanide/formaldehyde to amine is suitable since much of the cyanide/formaldehyde is lost to by-product glycolate and formate. The method may be carried out as a batch or as a continuous process, the latter using, for example, a continuous stirred-tank reactor (CSTR).

It has been found that chelants prepared by the methods of the invention contain lower levels of NTA than materials prepared by the conventional methods. In some embodiments, chelants may be prepared that contain 5.5 percent or less, alternatively 3 percent or less, alternatively 2 percent or less, alternatively 1.5 percent or less, or alternatively 1 percent or less of NTA (or its salts), based on the total weight of NTA and chelant, or salts thereof, as determined for instance by HPLC.

By way of illustration, an EDTA product containing low levels of NTA may suitably be obtained in a batch process, as follows. One mole of ethylene diamine may be mixed with 0.1-0.3, alternatively 0.16, moles of sodium hydroxide (e.g., in the form of a 50% NaOH solution) and the temperature elevated, for instance to 60-100° C., alternatively to 70° C. Cyanide, 1.9 to 2.0 moles, alternatively 1.95 moles, and formaldehyde, 1.9 to 2.1 moles, alternatively 1.99 moles, are added at a constant rate over 1 to 3 hours, alternatively 2 hours, which may result in the mixture heating to boiling temperatures. Another 1.9 to 2.0 moles, alternatively 1.95 moles, of cyanide and 1.9 to 2.1 moles, alternatively 1.99 moles, of formaldehyde are added at a substantially constant rate over 3 to 5 hours, alternatively 4 hours, to complete the reaction. At the start and throughout the reaction, ammonia is substantially removed, for instance by steam distillation. Upon completion of the addition of the formaldehyde and cyanide, the reaction may be boiled for an additional period, e.g., 1 to 3 hours, alternatively 2 hours, to remove remaining ammonia. Typical workup may be used to isolate the low NTA product.

The EDTA prepared by this process may contain 2 percent or less, alternatively 1.5 percent or less, or alternatively 1 percent or less of NTA (or its salts), based on the total weight of NTA and EDTA or their salts.

The method is not limited to formation of EDTA containing low amounts of NTA and indeed can be used for other chelants. The amine precursor for any particular chelant in the method can be readily determined by a person of ordinary skill in the art. Suitable precursors include primary or secondary amines (either cyclic or acyclic) such as diamines, triamines higher amines, amino alcohols, amino acids, amino thiols, aminosuccinates, polycarboxylate amines, amino ethers, substituted and unsubstituted guanidines, polyamino ethers, amino sugars, and chitosan. Also suitable are materials that hydrolyze under the reaction conditions into an amine, such as: amides, cyclic amides, imines and imides.

The cyanide used in the reaction may be in the form of a cyanide salt (e.g., sodium cyanide) or hydrogen cyanide. In addition, glycolonitrile may be used as a substitute for cyanide and formaldehyde (glycolonitrile is the reactive product obtained when cyanide and formaldehyde are mixed together).

The terms "carboxylic acid," "acid," "aminocarboxylic acid," and their derivations are used herein as shorthand to represent molecules containing these functional groups.

The following examples are illustrative of the invention but are not intended to limit its scope. Unless otherwise indicated, the ratios, percentages, parts, and the like used herein are by weight.

EXAMPLES

Example 1

Batch Synthesis of EDTA 1-mol of ethylenediamine (60.0-g) is mixed with 0.18-mol sodium hydroxide (14.7-g of 50% NaOH) and raised to 70° C. 4.47-mol of sodium cyanide (729.6-g of 30% aq sln) and 4.55-mol of formaldehyde (273.2-g of 50% aq sln) are added at a constant rate over 4.5-hrs and the reaction is allowed to quickly reach boiling temperature (materials can be obtained at Sigma-Aldrich). Any vapors escaping from the reaction are refluxed back to the reactor for the first half of the addition. After the first half of the addition, vapors are no longer refluxed, but distilled away from the reactor. Upon completion of the addition, the reaction is boiled for 2-hrs to remove any excess ammonia. 222.2-mol of water (151.3-g) are added back to the reaction and the reaction is cooled to room temperature. The resulting product contains 39.90-wt % tetrasodium ethylenediaminetetraacetate (Na4EDTA) and 2.5-wt % trisodium nitrilotriacetate (Na3NTA), as determined by HPLC analysis (see method below).

Example 2

Batch Synthesis of EDTA Containing Low Level of NTA 1-mol of ethylenediamine (60.0-g) is mixed with 0.16-mol sodium hydroxide (12.8-g of 50% NaOH) and raised to 70° C. 1.95-mol of sodium cyanide (318.4-g of 30% aq sln) and 1.99-mol of formaldehyde (119.2-g of 50% aq sln) are added at a constant rate over 2-hrs, quickly allowing the mixture to heat to boiling temperatures. At the start of the addition and throughout the reaction, steam is used to distill off the ammonia. Another 1.95-mol of sodium cyanide (318.4-g of 30% aq sln) and 1.99-mol of formaldehyde (119.2-g of 50% aq sln) are added at a constant rate over 4-hrs to complete the reaction. Upon completion of the addition, the reaction is boiled for 2-hrs to remove any excess ammonia. 222.2-mol of water (151.3-g) are added back to the reaction and the reaction is cooled to room temperature. The resulting product contains 39.24-wt % Na4EDTA and 0.4-wt % Na3NTA, as determined by HPLC analysis.

Example 3

Free Flowing Solid EDTA

Four aqueous solutions containing 39-wt % $Na_4EDTA$ are adjusted to different excess caustic levels, such that the solutions contain 0.0-wt %, 0.4-wt %, 0.8-wt %, and 1.3-wt % excess sodium hydroxide. The 0.0-wt % excess caustic solution is prepared by dissolving 50.5-g of EDTA acid into 2134.8-g of solution containing 39-wt % $Na_4EDTA$ and 1.30-wt % excess NaOH and then diluting with 101.9-g of water. The 0.4-wt % excess NaOH is prepared by mixing 155.8-g of the 0.0-wt % NaOH solution with 76.9-g of the 1.3-wt % NaOH solution. The 0.8-wt % excess NaOH solution is prepared by mixing 160-g of the 1.3-wt % NaOH solution with 85.2-g of the 0.0-wt % NaOH solution, The solutions are spray dried on a Buchi benchtop spray drier using a two-fluid nozzle atomizer at the same conditions for each (3.1-mL/min liquid rate, 24M-L/hr gas rate, 200° C. inlet air, and 580-L/hr nozzle air). The resulting powders have similar particle sizes and initial moisture levels (7-wt % water). The four powders are tested for flowability using an RST-Control 95 SX shear cell tester, which measures the yield strength gained by the sample under varying degrees of consolidating stress. There is a distinct trend for powder with higher excess caustic levels to have a higher resistance to flow (greater gain in yield strength), which becomes more pronounced at higher stress levels. FIG. 1 is a graph showing the flowability curves for the material under various loads.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A method for producing a free-flowing solid aminocarboxylate chelant, the method comprising:

(a) providing a solution comprising the aminocarboxylate chelant and residual alkaline metal hydroxide;
(b) adding to the solution a free or partially neutralized carboxylic acid such that the free or partially neutralized acid neutralizes at least a portion of the residual alkaline metal hydroxide; and
(c) isolating therefrom the free-flowing solid aminocarboxylate chelant, wherein the amount of free or partially neutralized carboxylic acid added in step (b) is such that no more than 5% by weight of the aminocarboxylate chelant is acidified.

2. A method according to claim 1 wherein the free-flowing solid aminocarboxylate chelant is isolated under step (c) by crystallization.

3. A method according to claim 1 wherein the free-flowing solid aminocarboxylate chelant is isolated under step (c) by drying.

4. A method according to claim 1 wherein the free-flowing solid aminocarboxylate chelant is isolated under step (c) by spray drying, rotating disk drying, rotating drum drying, freeze drying, or vacuum oven drying.

5. A method according to claim 1 wherein sufficient free or partially neutralized carboxylic acid is added such that the concentration of residual alkaline metal hydroxide is 2% or less by weight, based on the total weight of the solution.

6. A method according to claim 1 wherein the aminocarboxylate chelant is ethylenediamine-N,N,N',N'-tetraacetic acid tetrasodium salt, 1,1,4,7,7-diethylene-triaminepentaacetic acid pentasodium salt, ethylenediamine- N,N'-disuccinic acid disodium salt, (2-hydroxyethyl)-imino-diacetic acid disodium salt, L-glutamic acid-N,N-di-(acetic acid) tetrasodium salt, ethylenediamine-N,N'-diacetic acid disodium salt, or hydroxyethylethylene-diaminotriacetic acid trisodium salt.

7. A method according to claim 1 wherein the free or partially neutralized carboxylic acid is oxalic acid, glycolic acid, or formic acid.

8. A method according to claim 1 wherein the free or partially neutralized carboxylic acid comprises: ethylenediamine-N,N,N',N'-tetraacetic acid (EDTA), 1,1,4,7,7-diethylene-triaminepentaacetic acid (DTPA), ethylenediamine-N,N'-disuccinic acid (EDDS), (2-hydroxyethyl)-imino-diacetic acid (HEIDA), L-glutamic acid-N,N-di-(acetic acid) (GLDA), ethylenediamine-N,N'-diacetic acid (EDDA), hydroxyethylethylene-diaminotriacetic acid (HEDTA), or a partial salt of any of the foregoing.

9. A method for producing free-flowing solid ethylenediamine-N,N,N',N'-tetraacetic acid tetrasodium salt ($Na_4EDTA$), the method comprising:
(a) providing a solution comprising the ethylenediamine-N,N,N',N'-tetraacetic acid tetrasodium salt and residual sodium hydroxide;
(b) adding to the solution ethylenediamine-N,N,N',N'-tetraacetic acid or a partial salt thereof such that at least a portion of the residual sodium hydroxide is neutralized; and
(c) isolating therefrom the free-flowing solid ethylenediamine-N,N,N',N'-tetraacetic acid tetrasodium salt by crystallization or spray-drying,
wherein the amount of ethylenediamine-N,N,N',N'-tetraacetic acid or a partial salt thereof added in step (b) is such that no more than 5% by weight of the ethylenediamine-N,N,N',N'-tetraacetic acid tetrasodium salt is acidified.

* * * * *